United States Patent [19]

Sih

[11] 4,288,606
[45] Sep. 8, 1981

[54] ESTERS OF PROSTACYCLIN-TYPE COMPOUNDS

[75] Inventor: John C. Sih, Kalamazoo, Mich.

[73] Assignee: The Upjohn Company, Kalamazoo, Mich.

[21] Appl. No.: 121,844

[22] Filed: Feb. 15, 1980

Related U.S. Application Data

[62] Division of Ser. No. 48,496, Jun. 14, 1979, Pat. No. 4,236,019, which is a division of Ser. No. 933,329, Aug. 14, 1978, Pat. No. 4,180,657.

[51] Int. Cl.³ .......................................... C07C 177/00
[52] U.S. Cl. .......................................... 560/8; 560/51; 560/53; 560/60; 560/61
[58] Field of Search ................... 560/119, 8, 51, 53, 560/60, 61; 562/500

[56] References Cited

FOREIGN PATENT DOCUMENTS 2013601  2/1979  United Kingdom ................ 560/119

Primary Examiner—Robert Gerstl
Attorney, Agent, or Firm—Robert A. Armitage

[57] ABSTRACT

Acyl-substituted phenyl esters of prostacyclin-type compounds, for example the 4-acetylphenyl ester of prostacyclin ($PGI_2$) illustrated by the formula

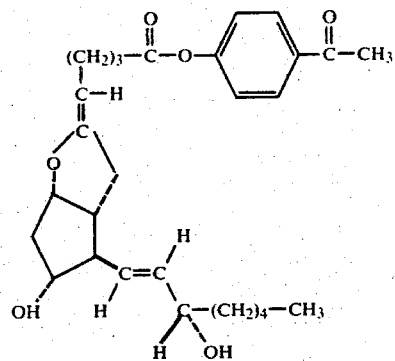

and including esters of the isomeric 6-hydroxy-$PGI_2$ and 6-keto-$PGF_{1\alpha}$ compounds, said esters having pharmacological activity. Processes for preparing them and the appropriate intermediates are disclosed.

1 Claim, No Drawings

ESTERS OF PROSTACYCLIN-TYPE COMPOUNDS

The present application is a divisional application of Ser. No. 048,496, filed 14 June 1979; which in turn is a divisional application of Ser. No. 933,329, filed 14 Aug. 1978, now issued as U.S. Pat. No. 4,180,657, on 25 Dec. 1979.

The present invention relates to prostaglandin analogs for which the essential material constituting a disclosure therefor is incorporated by reference here from U.S. Pat. No. 4,180,657, issued 25 Dec. 1979.

We claim:

1. An acid ester of a 6a-carba prostacyclin analog of the formula

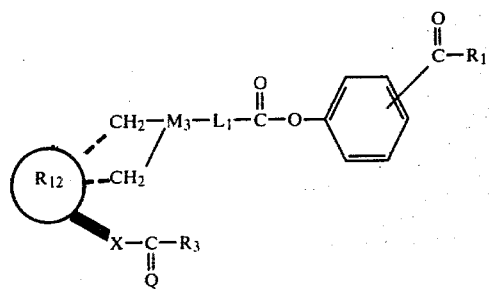

wherein $L_1$ is
  (1) —$(CH_2)_n$— wherein n is one to 5, inclusive,
  (2) —$(CH_2)_p$— wherein p is 2, 3, or 4, or
  (3) —$(CH_2)_v$—CH=CH— wherein v is 1, 2, or 3,
wherein $M_3$ is

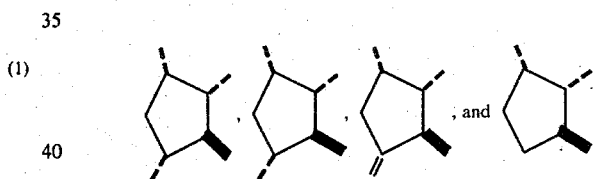

wherein Q is oxo, α-H:β-H, α-OH:β-$R_4$, or α-$R_4$:β-OH, wherein $R_4$ is hydrogen or alkyl of one to 4 carbon atoms, inclusive, wherein $R_1$ alkyl of one to 4 carbon atoms with the proviso that when $R_1$ is tert-butyl the group

is in the 4-position,
wherein $R_3$ is

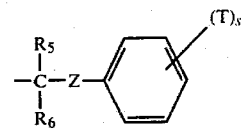

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; and the further proviso that neither $R_5$ nor $R_6$ is fluoro when Z is oxa (—O—);

wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive and s is zero, one, 2, or 3, with the proviso that not more than two T's are other than alkyl and when s is 2 or 3 the T's are either the same or different.

wherein $R_{12}$ is

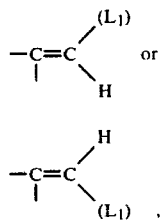

wherein X is
  (1) trans—CH=CH—
  (2) cis—CH=CH—
  (3) —C≡C— or
  (4) —$CH_2CH_2$—.

UNITED STATES PATENT OFFICE
CERTIFICATE OF CORRECTION

Patent No. 4,288,606   Dated 8 September 1981

Inventor(s) John C. Sih

It is certified that error appears in the above-identified patent and that said Letters Patent are hereby corrected as shown below:

Column 2, lines 35-42,

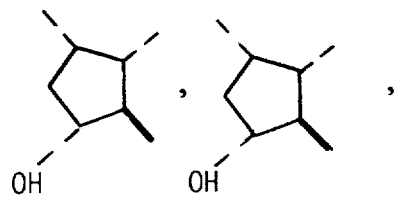 should read 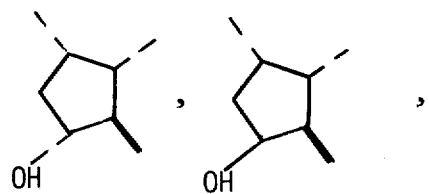

Signed and Sealed this

Ninth Day of February 1982

[SEAL]

Attest:

GERALD J. MOSSINGHOFF

Attesting Officer   Commissioner of Patents and Trademarks